(12) United States Patent
Hake et al.

(10) Patent No.: US 11,990,214 B2
(45) Date of Patent: May 21, 2024

(54) HANDLING FORM DATA ERRORS ARISING FROM NATURAL LANGUAGE PROCESSING

(71) Applicant: International Business Machines Corporation, Armonk, NY (US)

(72) Inventors: Paul Joseph Hake, Madison, CT (US); Igor S. Ramos, Round Rock, TX (US); Andrew J. Lavery, Austin, TX (US); Scott Carrier, New Hill, NC (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 379 days.

(21) Appl. No.: 16/934,061

(22) Filed: Jul. 21, 2020

(65) Prior Publication Data

US 2022/0028502 A1    Jan. 27, 2022

(51) Int. Cl.
| | | |
|---|---|---|
| *G16H 10/60* | (2018.01) | |
| *G06F 16/93* | (2019.01) | |
| *G06F 18/20* | (2023.01) | |
| *G06F 18/214* | (2023.01) | |
| *G06F 18/24* | (2023.01) | |
| *G06F 40/20* | (2020.01) | |
| *G06V 10/22* | (2022.01) | |
| *G06V 30/40* | (2022.01) | |

(Continued)

(52) U.S. Cl.
CPC ............. *G16H 10/60* (2018.01); *G06F 16/93* (2019.01); *G06F 18/214* (2023.01); *G06F 18/24* (2023.01); *G06F 18/285* (2023.01); *G06F 40/20* (2020.01); *G06V 10/22* (2022.01); *G06V 30/40* (2022.01); *G16H 15/00* (2018.01); *G16H 50/70* (2018.01)

(58) Field of Classification Search
CPC ........ G16H 10/60; G16H 50/70; G06F 40/20; G06V 30/40; G06K 9/62
See application file for complete search history.

(56) References Cited

U.S. PATENT DOCUMENTS

| 5,664,109 | A | * | 9/1997 | Johnson | .................. | G16H 10/60 |
| | | | | | | 706/45 |
| 9,047,529 | B2 | | 6/2015 | Xue | | |
| 9,342,741 | B2 | | 5/2016 | Amtrup et al. | | |

(Continued)

FOREIGN PATENT DOCUMENTS

WO    WO-2020074786 A1 *    4/2020    ........... G06F 40/205

*Primary Examiner* — Mamon Obeid
*Assistant Examiner* — Chance L Smith
(74) *Attorney, Agent, or Firm* — Cantor Colburn LLP; Kelsey M. Skodje

(57) ABSTRACT

Aspects include receiving a document and classifying at least a subset of the document as having a first type of data. Features are extracted from the document. The extracting includes initiating processing of the at least a subset of the document by a first processing engine that was previously trained to extract features from the first type of data. The extracting also includes initiating processing of a remaining portion of the document not included in the at least a subset of the document by a second processing engine that was previously trained to extract features from a second type of data. The first type of data is different than the second type of data. Features are received from one or both of the first processing engine and the second processing engine. The received features are stored as features of the document.

24 Claims, 10 Drawing Sheets

(51) Int. Cl.
   *G16H 15/00*   (2018.01)
   *G16H 50/70*   (2018.01)

(56) References Cited

U.S. PATENT DOCUMENTS

| | | | |
|---|---|---|---|
| 9,785,627 | B2 | 10/2017 | Campanelli et al. |
| 10,614,266 | B2 | 4/2020 | Dakin et al. |
| 11,424,012 | B1* | 8/2022 | Rai ........................ G16H 10/60 |
| 2009/0138284 | A1* | 5/2009 | Guadagna ............. G16H 15/00 |
| | | | 382/187 |
| 2012/0004931 | A1* | 1/2012 | Thierman .............. G16H 10/20 |
| | | | 235/382 |
| 2018/0011922 | A1* | 1/2018 | Sethumadhavan .... G16H 50/70 |
| 2019/0252047 | A1* | 8/2019 | Boloor ................... G16H 50/20 |
| 2020/0143913 | A1* | 5/2020 | Castine ................... G06F 16/35 |
| 2020/0159820 | A1* | 5/2020 | Rodriguez ........... G06V 30/412 |
| 2020/0184267 | A1* | 6/2020 | Kumar ............. G06V 30/18057 |
| 2020/0243174 | A1* | 7/2020 | Burgess ................ G06F 40/205 |
| 2021/0141861 | A1* | 5/2021 | Kalluri ................. G06F 40/279 |
| 2021/0166014 | A1* | 6/2021 | Zhang ................. G06V 30/413 |
| 2021/0350516 | A1* | 11/2021 | Tang ....................... G06F 16/93 |

\* cited by examiner

FAMILY HISTORY: (circle all that have occurred in a blood relative and indicate relationship)

Migraine   Stroke   Seizures   Multiple Sclerosis   Alzheimer's Disease   Parkinson's Disease
Nerve/Muscle Disease   Tremor   Depression/Anxiety   Alcohol/Drug Abuse   Diabetes
High Blood Pressure  (Heart Disease)  Anemia   Thyroid Disease   Cancer   Arthritis
                      FATHER

FIG. 2

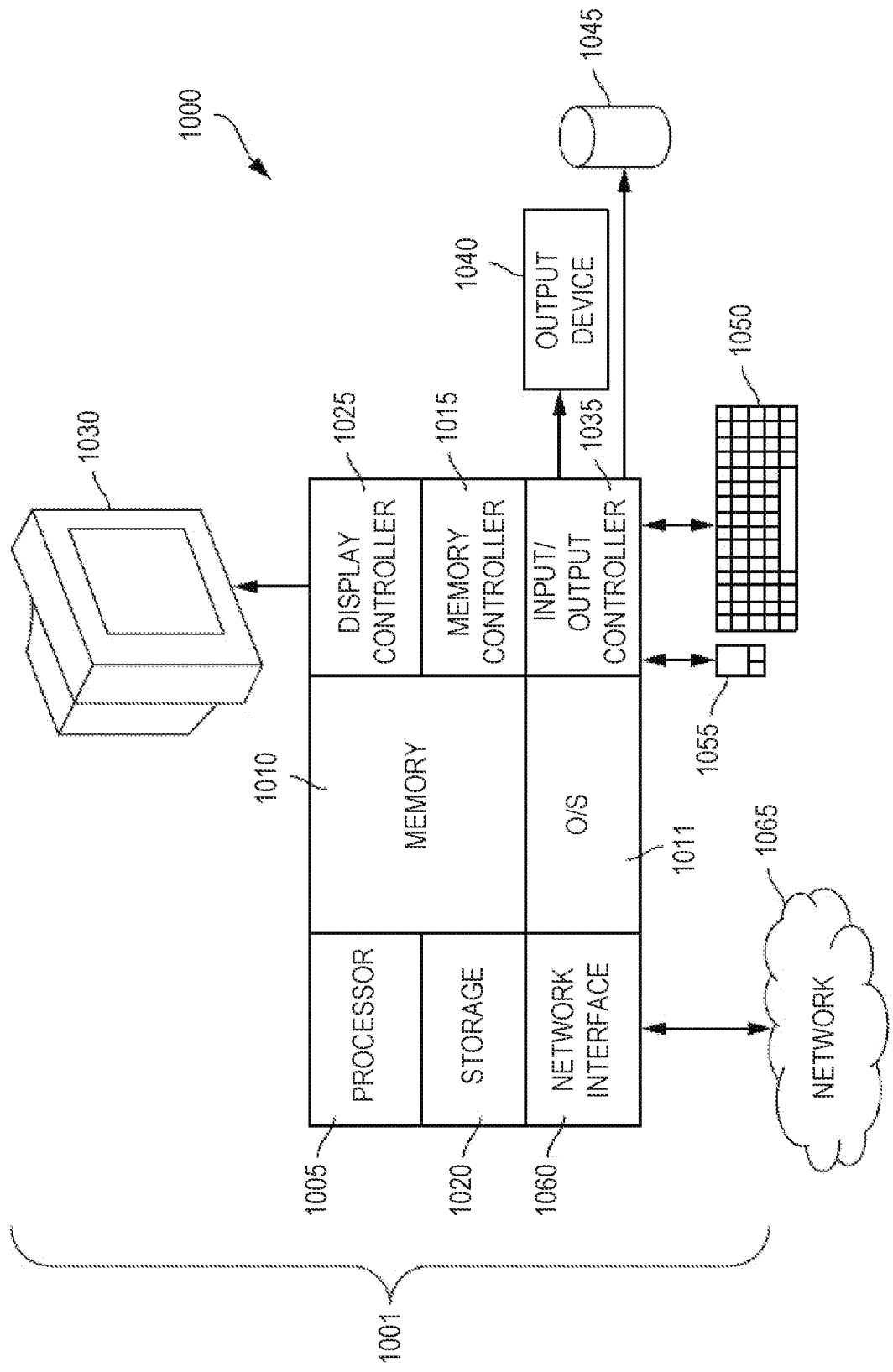

HANDLING FORM DATA ERRORS ARISING FROM NATURAL LANGUAGE PROCESSING

BACKGROUND

The present invention generally relates to natural language processing (NLP), and more specifically, to handling form data errors arising from NLP.

Machine learning is a form of artificial intelligence that uses algorithms to enable a system to learn from data rather than through explicit programing. Machine learning follows a process of preparing data, training an algorithm to generate a machine learning model, and then making and refining predictions. The field of machine learning has been gaining momentum due to the capabilities of state-of-the-art processors and to the abundant amount of digitized data that is available, which are both key to achieving accurate predictions.

NLP is a process that can leverage machine learning and can enable communication between computers and humans in natural language. With the massive amounts of data that are available and being added to computer repositories each day, companies are trying to figure out how they can structure the data, clean it, and garner deeper insights from the data. NLP is the parsing and semantic interpretation of text, allowing computers to learn, analyze, and understand human language. Machine learning algorithms learn from a labelled set of features from training data.

Visual recognition is another type of machine learning or deep learning which provides the ability to recognize, identify and/or understand visual information from visual content such as image data and video data. Optical character recognition (OCR) refers to the conversion of images of typed, handwritten or printed text into machine-encoded text, whether from a scanned document, a photo of a document, a scene-photo (for example the text on signs and billboards in a landscape photo) or from subtitle text superimposed on an image (for example from a television broadcast). OCR is widely used as a form of data entry from printed paper data records for digitizing printed texts so that they can be electronically edited, searched, stored more compactly, displayed on-line, and used in machine learning processes.

Healthcare documents, such as medical records, are an example of a type of digitized data that is stored in computer systems. NLP techniques can be used to extract features describing a patient from a medical record(s) associated with the patient such as a medical condition of the patient, a height of the patient, and/or a test performed or scheduled to be performed on the patient. Medical records can be stored in many different formats including text data and/or image data. In addition, medical records often include structure information such as titles, sections, and headers; as well as forms that may include lists of symptoms.

Inaccuracies can occur when performing feature extraction on medical records due to pages that contain forms being misinterpreted by conventional NLP techniques. For example, a form may include a questionnaire, or a list of symptoms or diseases for a patient to select from. Commonly found forms in medical records can cause issues where information such as lists of symptoms or diseases on the form appear to contemporary text processing (e.g., NLP and/or OCR) models as potential valid findings (false positives) as it may not be possible to identify the context of the text from the form. These issues are exacerbated by the variety of inconsistent manners of selecting items in a list of items.

SUMMARY

Embodiments of the present invention are directed to handling form data errors arising from natural language processing. A non-limiting example method includes receiving a document and classifying at least a subset of the document as having a first type of data. Features are extracted from the document. The extracting includes initiating processing of the at least a subset of the document by a first processing engine that was previously trained to extract features from the first type of data. The extracting also includes initiating processing of a remaining portion of the document not included in the at least a subset of the document by a second processing engine that was previously trained to extract features from a second type of data. The first type of data is different than the second type of data. Features are received from one or both of the first processing engine and the second processing engine. The received features are stored as features of the document.

One or more embodiments of the present invention are directed to a system for handling form data errors arising from NLP. A non-limiting example of the system includes a memory having computer-readable instructions and one or more processors for executing the computer-readable instructions. The computer-readable instructions may implement the above method.

One or more embodiments of the present invention are directed to a computer-program product for handling form data errors arising from NLP, the computer-program product including a computer-readable storage medium having program instructions embodied therewith. The program instructions are executable by a processor to cause the processor to perform the above method.

Thus, advantageously, different types of data contained in documents can be analyzed, and features extracted, using different processing engines that were trained for the specific types of data. This can lead more accurate feature extraction from documents.

Additionally, or alternatively to the above, the first type of data is form data and the second type of date is sentence or paragraph data. Thus, advantageously, feature extraction from documents that contain forms can be more accurate and can result in fewer false positives.

Additionally, or alternatively to the above, the received features are combined to generate combined features of the document, where the features of the document that are stored are the combined features of the document. Thus, advantageously, features from both types of data in the document can be combined.

Additionally, or alternatively to the above, the document is a healthcare document for a patient and the method further includes associating the received features with the patient. Thus, advantageously, information about a patient can be extracted from a health care document with a higher degree of accuracy.

Additionally, or alternatively to the above, the healthcare document is a medical record. Thus, advantageously, information about a patient can be extracted from a medical document with a higher degree of accuracy.

Additionally, or alternatively to the above, the processing by one or both of the first processing engine and the second processing engine includes NLP. Thus, advantageously different NLP engines can be applied to different types of data.

Additionally, or alternatively to the above, converting the document to a text format prior to the identifying. Thus, advantageously the classifying can be optimized for text formatted documents.

Additionally, or alternatively to the above, converting the document to an image format prior to the identifying. Thus, advantageously the classifying can be optimized for image formatted documents.

Additionally, or alternatively to the above, the classifying is performed by a classifier engine that was previously trained to identify the first type of data in documents. Thus, advantageously a trained classifier engine can be used to perform the classifying in a resource efficient manner.

Additionally, or alternatively to the above, a second document that does not include the first type of data is received. Features are extracted from the second document. The extracting includes initiating processing of the second document by the second processing engine; receiving second features from the second processing engine; and storing the received second features as features of the second document. Thus, advantageously, features can be extracted from a document using a single processing engine.

One or more embodiments of the present invention are directed to a method for handling form data errors arising from NLP. A non-limiting example of the method includes receiving a document that includes a form and determining a style of the form. An NLP engine is selected based at least in part on the style of the form, where the selected NLP engine was previously trained to extract features from forms having the determined style. Processing of the form by the selected NLP engine is initiated.

Thus, advantageously, different types of forms can be handled differently, which can lead to more accurate feature extraction from documents that contain forms.

Additionally, or alternatively to the above the determining the style of the form is performed by a classifier engine that was previously trained to identify styles of forms. Thus, advantageously. a trained classifier engine can be used to perform the classifying in a resource efficient manner Additionally, or alternatively to the above the style is a check box style form. Thus, advantageously features can be extracted more accurately from check box style forms.

Additionally, or alternatively to the above the style is a circle applicable conditions style form. Thus, advantageously features can be extracted more accurately from circle applicable conditions style form.

Additionally, or alternatively to the above the style is a radio button style form. Thus, advantageously features can be extracted more accurately from radio button style form.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIG. 2 depicts an example of a medical form that includes a list of medical conditions and a request to circle any that a blood relative of a patient has had as well as a request to indicate the relationship between the patient and the blood relative;

FIG. 10 illustrates a system for handling form data according to one or more embodiments of the present invention.

Figure 1:
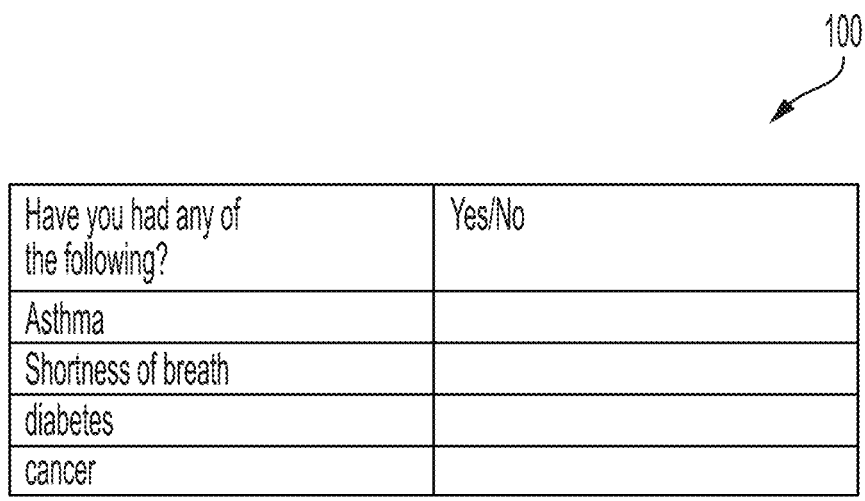
FIG. 1 depicts an example of a medical form that includes a table with a list of symptoms/medical conditions and a box for indicating whether a patient exhibits each symptom/medical condition.

The diagrams depicted herein are illustrative. There can be many variations to the diagrams, or the operations described therein without departing from the spirit of the invention. For instance, the actions can be performed in a differing order or actions can be added, deleted or modified. Also, the term "coupled", and variations thereof describe having a communications path between two elements and do not imply a direct connection between the elements with no intervening elements/connections between them. All of these variations are considered a part of the specification.

DETAILED DESCRIPTION

One or more embodiments of the present invention are directed to applying different natural language processing (NLP) models to different portions of a document based on the type of data contained in the different portions of the document. In accordance with one or more embodiments of the present invention, a portion(s) that includes form data and a portion(s) that contains sentence or paragraph data, are identified within a document. Any page or section within a page of a document that contains a form is processed with a distinct sub-process trained exclusively to extract features from form-style data, and the rest of the document is processed by an NLP engine trained to extract features from sentence or paragraph data. Routing the portions of the document that have been identified as including a form, or form data, to a separate NLP model that is trained exclusively on form-style data can result in more accurate feature extraction from documents that contain forms. One or more embodiments of the present invention can operate on image data and/or text data to identify forms within a document.

As described above, healthcare records are an example of digitized documents that are stored in computers. Healthcare documents can include, but are not limited to medical records, lab reports, pathology reports, and pre-authorization forms. Healthcare documents can be used by medical practitioners to understand the medical history, or previous health status, of the patient, as well as to keep the medical practitioner up to date about the patient's current status in order to aid the medical practitioner in providing the patient with optimal healthcare. Healthcare documents can also be analyzed by NLP engines to provide predictions about the future health state of a patient and/or to provide trends or predictions related to a group of patients. These trends or predictions can be based on current patient status and/or include predicted outcomes associated with various medical treatments that may be provided to the patient.

In accordance with one or more embodiments of the present invention, NLP techniques are used to extract features (e.g., facts) about a patient from one or more healthcare documents that are associated with the patient. Information in the healthcare documents can be entered by the patient and/or by the doctor. In addition, or alternatively, information in the healthcare documents can be provided automatically as part of a form for the doctor or patient to fill out, or as an output from a test (e.g., a blood test result or MRI image). The healthcare documents can be in a text format and/or an image format.

The terms "record" and "document" are used interchangeably herein to refer to a grouping of digitized data that is stored by a computer and processed as a single unit. A record or document may have one or more portions containing form data and one or more portions containing sentence or paragraph data. A portion includes a least a subset of the record or document.

As used herein, the term "form data" refers to data that includes a form(s). Forms in the medical field can include, for example, questions that include a list of symptoms, a questionnaire with a list of questions, and/or a list of medical conditions with an instruction to circle all that apply. Non-limiting examples of form data and styles of forms are described below in reference to FIGS. 1-3.

As used herein, the term "sentence or paragraph data" refers to a group of one or more text characters (e.g., natural language data) which may be grouped for example, into sentences or paragraphs.

As used herein, the term "NLP engine" refers to software and/or hardware components that process and analyze natural language data (written and/or spoken). For written data, the natural language data that is input to the NLP engine can be grouped into documents which may include, for example, one or more sentences, one or more paragraphs, one or more forms, and/or one or more pages. The terms "trained NLP engine" or "NLP engine that has been trained" are used interchangeably herein to refer to an NLP engine that has been programmed to analyze a particular aspect(s) of the input documents. One or more embodiments of the present invention described herein include a form NLP engine which has been trained using form data as training data to extract features having to do with a health condition or status of a patient, and a sentence or paragraph NLP engine which has been trained using data grouped into sentences or paragraphs as training data, to extract features having to do with a health condition or status of a patient.

Contemporary methods of extracting features from a document include inputting the entire document into a trained NLP engine. This can result in inaccuracies in the extracted features when the documents include a mixture of data types, for example a mixture of form data, and sentence or paragraph data. The data within the forms can be misinterpreted by a conventional NLP engine. For example, commonly found forms in healthcare records can cause issues where information such as lists of symptoms or diseases on the form appear to text processing models such as NLP engines and/or optical character recognition (OCR) models as potential valid finding because it is difficult to identify the context from the form. The extracted features will contain false positives because each symptom in the list of symptoms will be interpreted as applying to the patient.

One or more embodiments of the present invention address one or more of the above noted shortcomings of contemporary approaches by utilizing a document classifier to classify portions of a document and then routing the portions of the document to different downstream NLP processors, or engines, based on the identified classes. In this manner, the portion of a healthcare record having form data will be analyzed differently than the portion of the healthcare record having sentence or paragraph data. This can result in faster processing with less computer resources as each of the NLP engines are targeted to a specific type of data. One or more embodiments of the present invention can generate extracted features that are a more accurate reflection of the patient due, for example, to having fewer false positives of symptoms and/or health conditions. In addition, in one or more embodiments of the present invention, when different NLP engines are used for different form styles, each NLP engine can be trained on any expected manners of selecting items on forms having the specific form style. Training for each specific type of form can allow the NLP engines to extract additional features with a higher level of certainty from form data.

Figure 3:
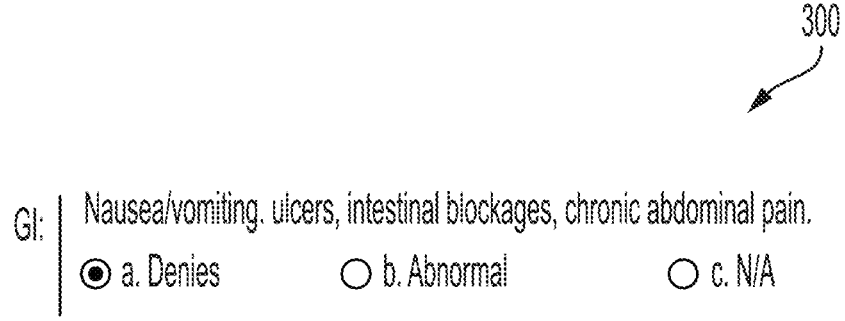
FIG. 3 depict an example of a medical form that includes a list of symptoms and radio buttons to indicate the applicability of the entire list of symptoms to a patient.

FIGS. 1-3 show examples of a few types of forms commonly found in healthcare records.

FIG. 1 is an example of a medical form 100 that includes a table with a list of symptoms/medical conditions and a box for indicating whether a patient exhibits each symptom/medical condition. The medical form 100 shown in FIG. 1 includes a list of symptoms and medical conditions which will be identified by text processing models such as OCR and/or NLP as potential valid findings (e.g., characteristics of a patient) as it is challenging to identify the context from the medical form 100. In addition, the recording of the "yes/no" response can be inconsistent depending on who is filling out the form. The recording can include for example, writing the word yes or the word no, leaving the space blank if the answer is no and putting a check in the box if the answer is yes, underlining or circling the symptom or medical condition if the answer is yes, and/or crossing out the symptom or medical condition if the answer is no.

One or more embodiments of the present invention can process the medical form 100 shown in FIG. 1 by classifying the form as a check box style form and then using an NLP engine that has been trained to operate on check box style forms. For example, the NLP engine can be trained to recognize the various methods of recording which symptoms or medical conditions apply to the patient being described in the document that contains the form. In accordance with one or more embodiments of the present invention, the NLP engine can be a distinct annotator that is highly conservative (high precision) in identifying diagnoses based on mentions on a form that includes a list. Being conservative can lead to fewer false positives (e.g., assigning a symptom or medical condition to a patient in error). In addition, if the form is known to be a type that is filled out by a patient the results of the NLP can be given less weight than data recorded by physicians or providers. All or a portion of the features output by the NLP engine can be discarded based on an assessment by the NLP of their accuracy.

Turning now to FIG. 2, an example of a medical form 200 that includes a list of medical conditions and a request to circle any that a blood relative of a patient has had, as well as a request to indicate the relationship between the patient and the blood relative, is generally shown. Similar to the medical form 100 of FIG. 1, the medical form 200 shown in FIG. 2 includes a list of medical conditions which could lead to false positives if the same NLP engine is used to process the medical form as is used to process sentence or paragraph data. In addition, the writing on the form can be difficult to interpret and/or it may make the medical conditions difficult to read. One or more embodiments of the present invention can process the medical form 200 shown in FIG. 2 by classifying the form as a circle applicable conditions style form and then using an NLP engine that has been trained to operate on circle applicable conditions style forms. All or a portion of the features output by the NLP engine can be discarded based on an assessment by the NLP of their accuracy.

Turning now to FIG. 3, an example of a medical form 300 that includes a list of symptoms and radio buttons to indicate the applicability of the entire list of symptoms to a patient is generally shown. One or more embodiments of the present invention can process the medical form 300 shown in FIG. 3 by classifying the form as a radio button style form and then using an NLP engine that has been trained to operate on radio button style forms. All or a portion of the features output by the NLP engine can be discarded based on an assessment by the NLP of their accuracy.

In accordance with one or more embodiments of the present invention, once a form is determined to be of a particular style (or the form does not have a recognized style), the portion of the document containing the form may be ignored and not input to the NLP of the document. This may occur for a variety of reasons, such as but not limited to, a NLP engine that has been trained to handle the form style is not available, or highly accurate results are required and the trained NLP engine is known to produce results that are below the accuracy threshold required.

As used herein, the terms accuracy of NLP or accuracy threshold of NLP refers to a likelihood (or probability) that a feature output from the NLP engine is correct. This can be assessed in a variety of manners such as, but not limited to precision, recall, and $F_1$ score.

Figure 4:
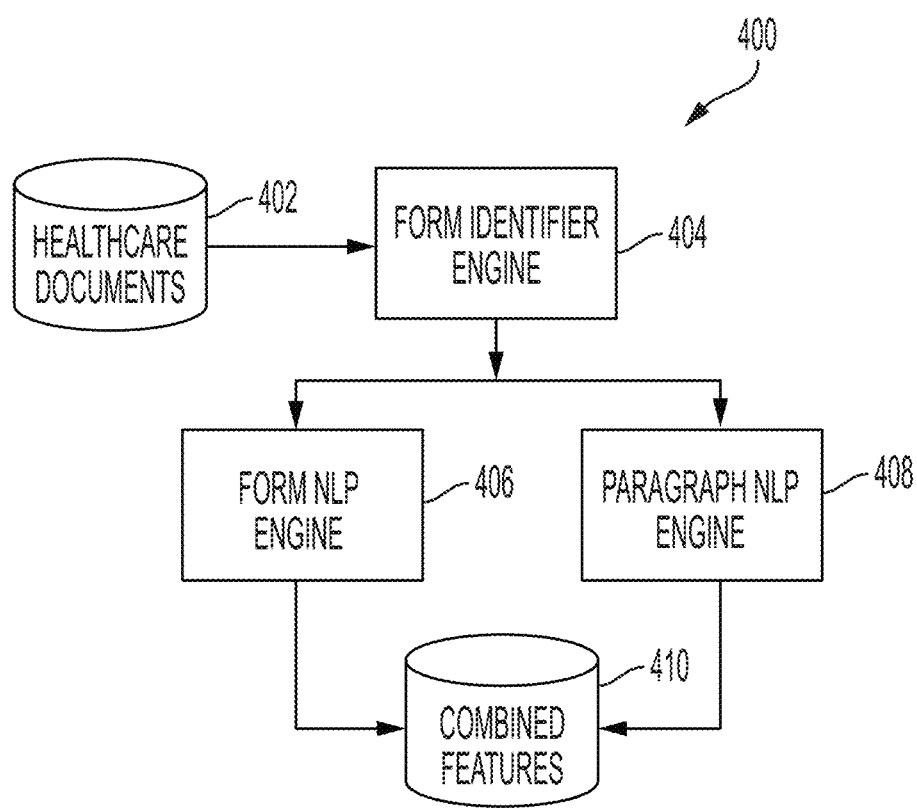
FIG. 4 depicts a block diagram of a system for handling form data in natural language processing (NLP) according to one or more embodiments of the present invention.

Turning now to FIG. 4, a block diagram 400 of a system for handling form data in NLP is generally shown in accordance with one or more embodiments of the present invention. The block diagram 400 shown in FIG. 4 includes healthcare documents 402, a form identifier engine 404, a form NLP engine 406, a paragraph NLP engine 408, and combined features 410. The healthcare documents 402 may be stored in a database or in any manner known in the art. As shown in FIG. 4, the healthcare documents 402 are input (e.g., one at a time) to form identifier engine 404. In accordance with one or more embodiments of the present invention, form identifier engine 404 performs a pre-processing step using, for example, image recognition to classify pages (or other portions or regions of a document) as containing form data. One or more embodiments of the present invention process the form pages differently than the non-form pages.

In one or more embodiments of the present invention, the healthcare documents 402 are stored in an image format and the form identifier engine 404 uses image recognition techniques to classify portions of the healthcare documents 402 as form data, or as paragraph data. In one or more embodiments of the present invention, the healthcare documents 402 are stored in a text format and the form identifier engine 404 uses text recognition techniques to classify portions of the healthcare documents 402 as form data, or as paragraph data. The form identifier engine 404 can look for particular phrases (e.g., "circle all that apply") or sequences or counts of characters (e.g., three or more radio buttons in the same paragraph) to classify portions of the healthcare documents 402 as form data.

In one or more embodiments of the present invention, some of the healthcare documents 402 are stored in an image format and others are stored in a text format, and the system shown in FIG. 4 also includes a format conversion engine (not shown) for converting the healthcare documents 402 (if needed) into an image format prior to inputting the healthcare documents 402 into the form identifier engine 404. In one or more alternate exemplary embodiments a format conversion engine converts the healthcare documents 402 (if needed) into a text format prior to inputting the healthcare documents 402 into the form identifier engine 404. In accordance with one or more embodiments of the present invention the form identifier engine 404 is implemented using machine learning or deep learning-based classifiers.

The training of the form identifier engine 404 can be performed using any manner known in the art. For example, the training data can include documents in image data format that contain one or more forms, as well as documents in image data format that do not contain forms. The form identifier engine 404 can be trained to identify the portion(s) of a healthcare document 402 that contains form data, and the identified portion(s) is sent to a form NLP engine 406 for processing. The remaining (non-form) portion(s) of the document 402 can be sent to paragraph NLP engine 408.

In accordance with one or more embodiments of the present invention, the form NLP engine 406 shown in FIG. 4 is trained to receive a portion of a healthcare document 402 that includes form data and to output features, or facts, about the patient associated with or being described by the healthcare document 402. In accordance with one or more embodiments of the present invention the form NLP engine 406 is implemented using feature extraction techniques or NLP feature extraction techniques including, but not limited to including dictionary or rule based as well as machine learning, deep learning or hybrid systems combining multiple techniques.

As described previously, in some cases, the form NLP engine 406 may output a limited number of features or may not output any features. In accordance with one or more embodiments of the present invention, for form NLP engine 406 is highly conservative (high precision) in identifying features as mentions on a form are highly likely to be lists. In addition, if the form is filled out by the patient, extracted features may be given less weight than features extracted from physician or provider documents. In accordance with one or more embodiments of the present invention if handwriting on a form or other marks are detected it could indicate that the extracted features are unreliable. In addition, in accordance with one or more embodiments, when a form-based list is identified and it has no indication(s) of selected items, no features will be output based on the list.

As shown in FIG. 4, form identifier engine 404 sends the non-form portion of the healthcare document 402 to paragraph NLP engine 408. In accordance with one or more embodiments of the present invention, the paragraph NLP engine 408 is trained to receive a portion of a healthcare document 402 that includes non-form data and to output features, or facts, about the patient associated with or being described by the healthcare document 402. In accordance with one or more embodiments of the present invention the paragraph NLP engine 408 is implemented using, for example, NLP feature extraction techniques including dictionary or rule based as well as machine learning, deep learning or hybrid systems combining multiple technique. In accordance with one or more embodiments of the present invention, a sentence NLP engine (not shown) is used in addition to or instead of paragraph NLP engine 408, where the sentence NLP engine is trained to receive data formatted into sentences and to output features based on the input. In one or more other embodiments of the present invention, a sentence or paragraph NLP engine (not shown) is used instead of the paragraph NLP engine 408, where the sentence or paragraph NLP engine is trained to input data formatted into sentences or paragraphs and to output features based on the input.

In accordance with one or more embodiments of the present invention, the form identifier engine 404, form NLP engine 406, and paragraph NLP engine 408 are implemented by any method known in the art such as, but not limited to application software executing on one or more servers and/or in containers. The training and processing of form identifier engine 404, form NLP engine 406, and paragraph NLP engine 408 can be executed by processor 1005 located on computer 1001 of FIG. 10 and/or by a processor located on a cloud computing node 10 of FIG. 8.

Any of the components shown in FIG. 4 may be coupled to each other via a network. For example, form identifier engine 404 may be coupled to form NLP engine 406 and paragraph NLP engine 408 via a network. The network(s) may be implemented by any network(s) known in the art such as, but not limited to a local area network (LAN), a direct cable connection, a cloud computing environment such as that shown below in FIG. 8, and/or the Internet.

The embodiments described herein with respect to block diagram 400 of FIG. 4 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various embodiments. In addition, the various blocks in FIG. 4 may be configured in different manners than that shown in FIG. 4. For example, the form identifier engine 404 may be implemented as two distinct processes executing on different processors, one process that classifies portions of the documents as containing forms and another process that transmits the portions of the documents to the correct NLP engine.

Figure 5:
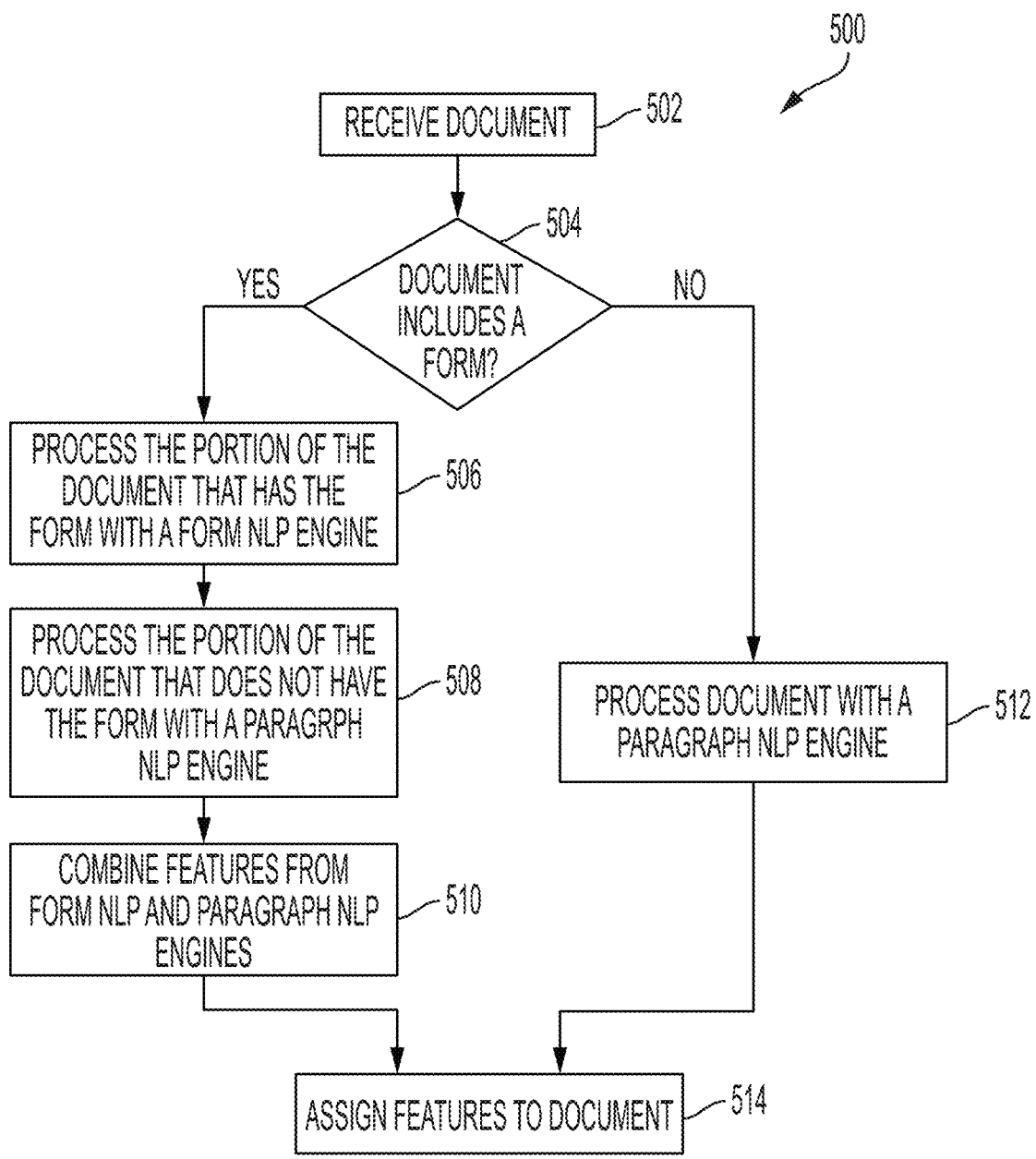
FIG. 5 depicts a flow diagram of handling form data in documents according to one or more embodiments of the present invention.

Turning now to FIG. 5, a flow diagram of a method 500 of handling form data in image documents is generally shown according to one or more embodiments of the present invention. The process shown in FIG. 5 starts at block 502 with receiving a document, such as a healthcare document 402 of FIG. 4. Processing continues at block 504 with determining whether the document includes a form. The processing at block 504 can be performed, for example by a classifier engine such as form identifier engine 404 of FIG. 4.

If it is determined at block 504 that the document includes a form, processing continues at block 506 with extracting features from the portion of the document having the form. Block 506 can be performed, for example by an NLP engine such as form NLP engine 404 of FIG. 4. Processing continues at block 508 with extracting features from the portion of the document that does not contain the form data. Block 508 can be performed using an NLP engine such as paragraph NLP engine 408 of FIG. 4.

At block 510 of FIG. 5, the features from the form NLP and the paragraph NLP are combined to create combined features for the document. The combining can be performed by computer instructions executing on processor 1005 located on computer 1001 of FIG. 10 or executing on a processor located on a cloud computing node 10 of FIG. 8. In accordance with one or more embodiments of the present invention, the form or list-based features are assumed to have or are assigned a lower confidence level of being accurate. Processing continues at block 514 with storing the combined features and/or assigning the features to the document (or to the patient associated with the document). Block 514 can be performed by computer instructions executing on processor 1005 located on computer 1001 of FIG. 10 or executing on a processor located on a cloud computing node 10 of FIG. 8.

If it is determined at block 504 that the document does not include a form, then processing continues at block 512 with extracting features from the document using an NLP engine such as paragraph NLP engine 408 of FIG. 4. At block 514, the features are stored and/or assigned to the document (or to the patient associated with the document).

The process flow diagram of FIG. 5 is not intended to indicate that the operations of the method 500 are to be executed in any particular order, or that all of the operations of the method 500 are to be included in every case. Additionally, the method 500 can include any suitable number of additional operations.

Figure 6:
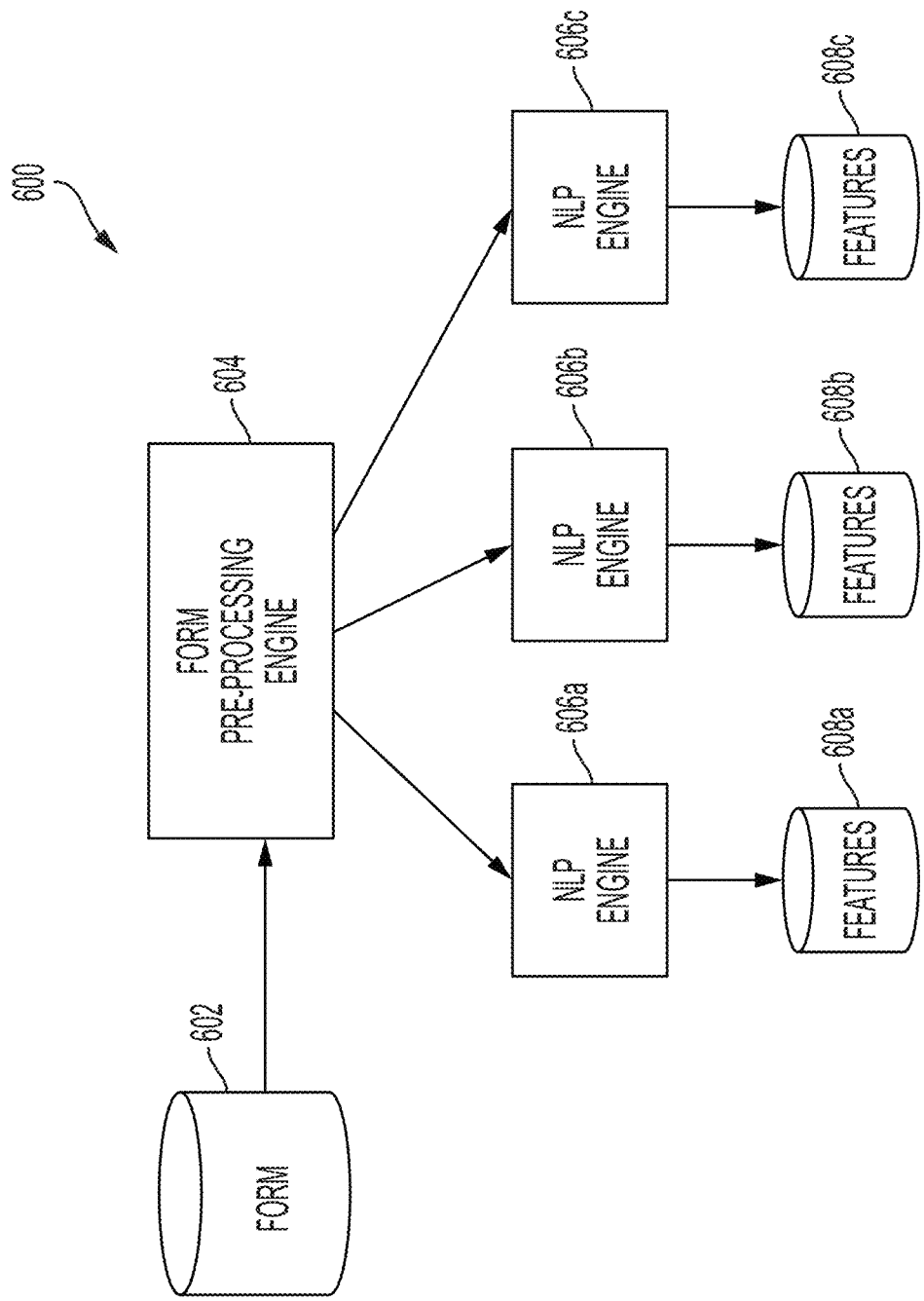
FIG. 6 depicts a block diagram of a system for handling form data in natural language processing (NLP) according to one or more embodiments of the present invention.

Turning now to FIG. 6, a block diagram 600 of a system for handling form data in NLP is generally shown in accordance with one or more embodiments of the present invention. The embodiment shown in FIG. 6, which includes a plurality of form NLP engines 606, provides another level of granularity when compared to the embodiment shown in FIG. 4, which includes a single form NLP engine 406.

The block diagram 600 shown in FIG. 6 includes forms 602 (or form data), form pre-processing engine 604, NLP engines 606a 606b 606c (collectively referred to herein as NLP engines 606), and features 608a 608b 608c (collectively referred to herein as features 608).

In accordance with one or more embodiments of the present invention, the forms 602 are the portion(s) of a document containing form data that are output from the form identifier engine 404 of FIG. 4. The embodiment shown in FIG. 6 includes a plurality of NLP engines 606 each trained to extract features from a particular form style. For example, NLP engine 606a can be trained to extract features 608a from check box style forms such as form 100 of FIG. 1, NLP engine 606b can be trained to extract features 608b from circle applicable conditions style forms such as form 200 of FIG. 2, and NLP engine 606c can be trained to extract features 608c from radio button style forms such as form 300 of FIG. 3. Having different NLP engines 606 each trained for a specific type of form can provide the ability to extract more features from a form and/or to have a higher level of confidence that the features are correct when compared to using a single NLP engine for extracting features from all styles of forms.

In accordance with one or more embodiments of the present invention, the form pre-processing engine 604 is included in the form identifier engine 404 of FIG. 4 and instead of the form identifier engine 404 sending all of the form data to a single form NLP engine 406, the form identifier engine 404 sends the form data to a particular NLP engine 606a 606b 606c depending on the style of the form. The features 608 output from the NLP engines 606 are input to the combined features 410 of FIG. 4.

In accordance with one or more embodiments of the present invention, the form pre-processing engine 604 and NLP engines 606 are implemented by any method known in the art such as, but not limited to application software executing on one or more servers and/or in containers. The training and processing of form pre-processing engine 604 and NLP engine 606 can be executed by processor 1005 located on computer 1001 of FIG. 10 and/or by a processor located on a cloud computing node 10 of FIG. 8.

Any of the components shown in FIG. 6 may be coupled to each other via a network. For example, form pre-processing engine 604 may be coupled to the NLP engines 606 via one or more networks. The network(s) may be implemented by any network(s) known in the art such as, but not limited to a local area network (LAN), a direct cable connection, a cloud computing environment such as that shown below in FIG. 8, and/or the Internet.

The embodiments described herein with respect to block diagram 600 of FIG. 6 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various embodiments. In addition, the various blocks in FIG. 6 may be configured in different manners than that shown in FIG. 6.

Figure 7:
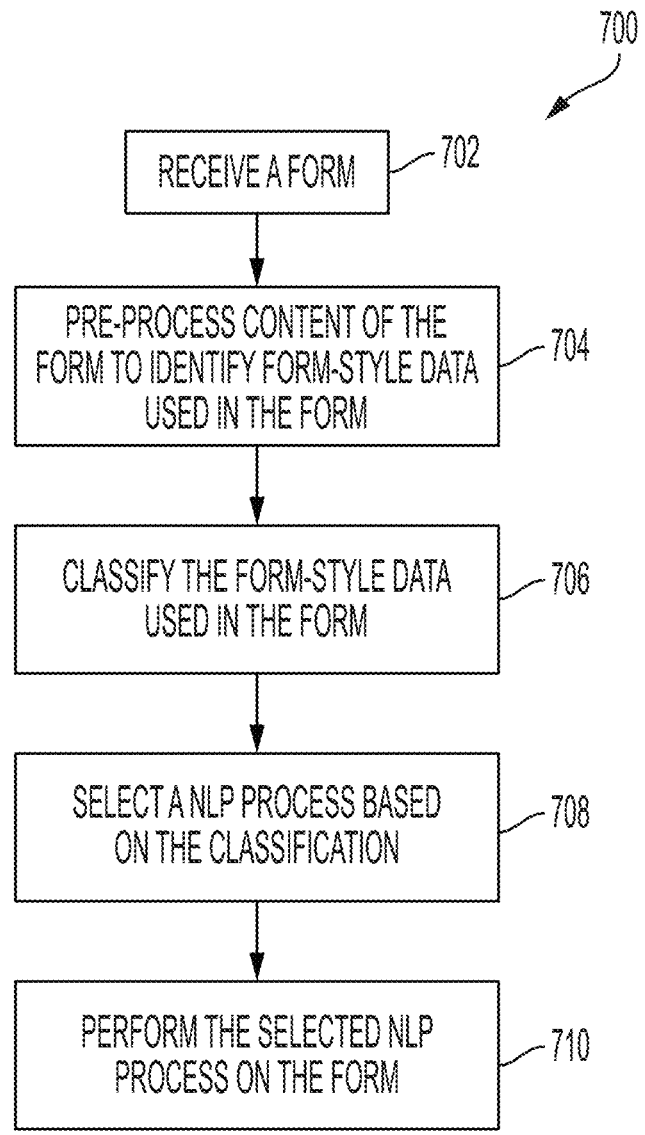
FIG. 7 depicts a flow diagram of handling form data in according to one or more embodiments of the present invention.

Turning now to FIG. 7, a flow diagram of a method 700 of handling form data is generally shown in accordance with one or more embodiments of the present invention. All or a portion of the processing shown in FIG. 7 can be performed, for example, by form pre-processing engine 604 executing on processor 1005 located on computer 1001 of FIG. 10 or executing on a processor located on a cloud computing node 10 of FIG. 8.

At block 702, a form such as form 602 is received. In accordance with one or more embodiments of the present invention, the form 602 is a portion of a healthcare document that is being analyzed using NLP to extract features. At block 704. The content of the form is processed to identify the form-style data used in the form. Examples of form-style data include but are not limited to questionnaires such as past medical history or current symptoms, mental state assessments, and medication lists At block 706, the form-style data is classified to identify a style of the form and at block 708 an NLP process is selected based on the classification, or style, of the form. In accordance with one or more embodiments of the present invention, the selected NLP process has been previously trained to extract features from forms having the identified form style of the form. At block 710, the selected NLP is performed on the form data to extract features.

The process flow diagram of FIG. 7 is not intended to indicate that the operations of the method 700 are to be executed in any particular order, or that all of the operations of the method 700 are to be included in every case. Additionally, the method 700 can include any suitable number of additional operations.

Examples described herein relate to healthcare documents which are just one type of document that may be input to one or more embodiments of the present invention. One skilled in the art will recognize that one or more embodiments of the present invention described herein can be applied to any type of documents that may contain form or other non-character string type data.

The examples described herein relate to form, and to sentence or paragraph data. One or more embodiments could also identify other types of data in documents for targeted NLP such as, but not limited to MRI data, laboratory reports or pathology reports.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third-party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third-party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
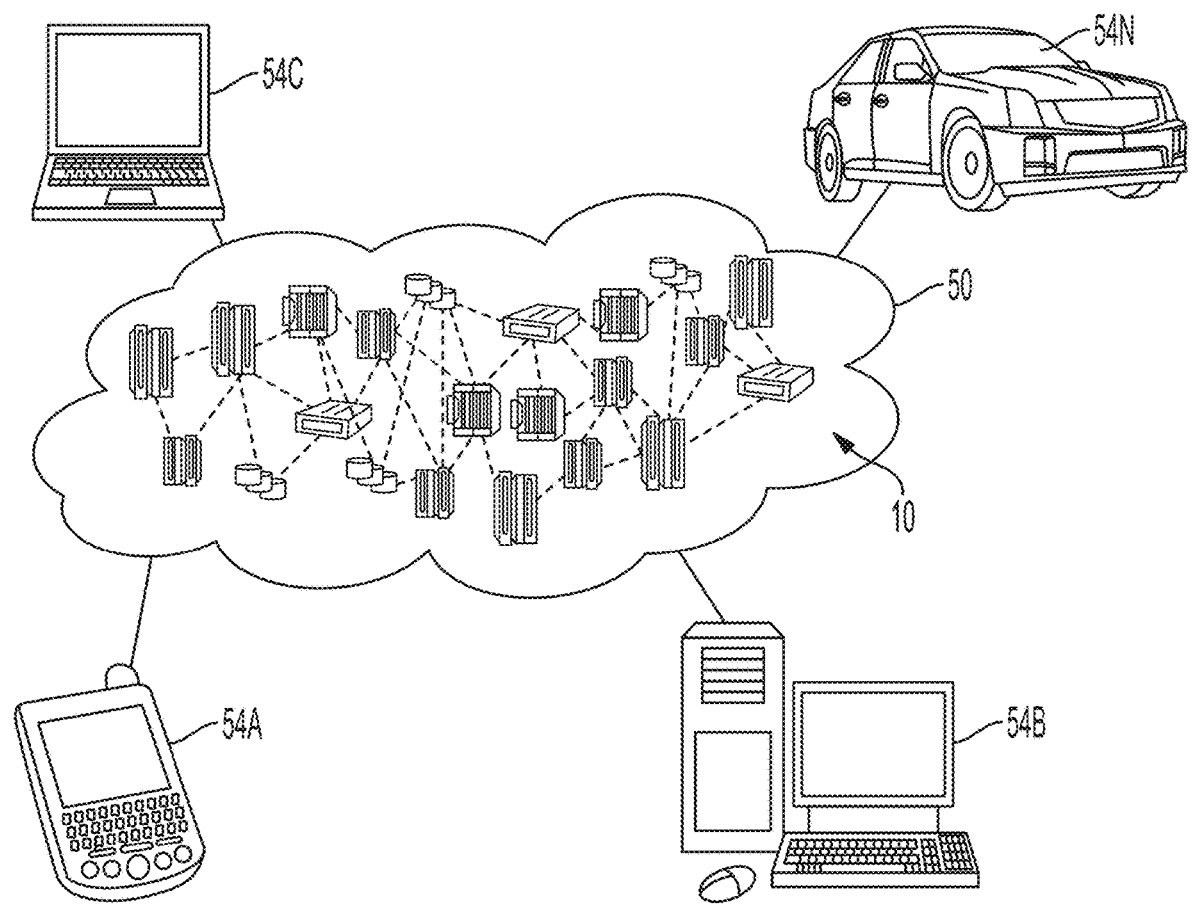
FIG. 8 depicts a cloud computing environment according to one or more embodiments of the present invention.

Referring now to FIG. 8, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 8 are intended to be illustrative only and that computing nodes 10 and cloud computing environment 50 can communicate with any type of computerized device over any type of network and/or network addressable connection (e.g., using a web browser).

Figure 9:
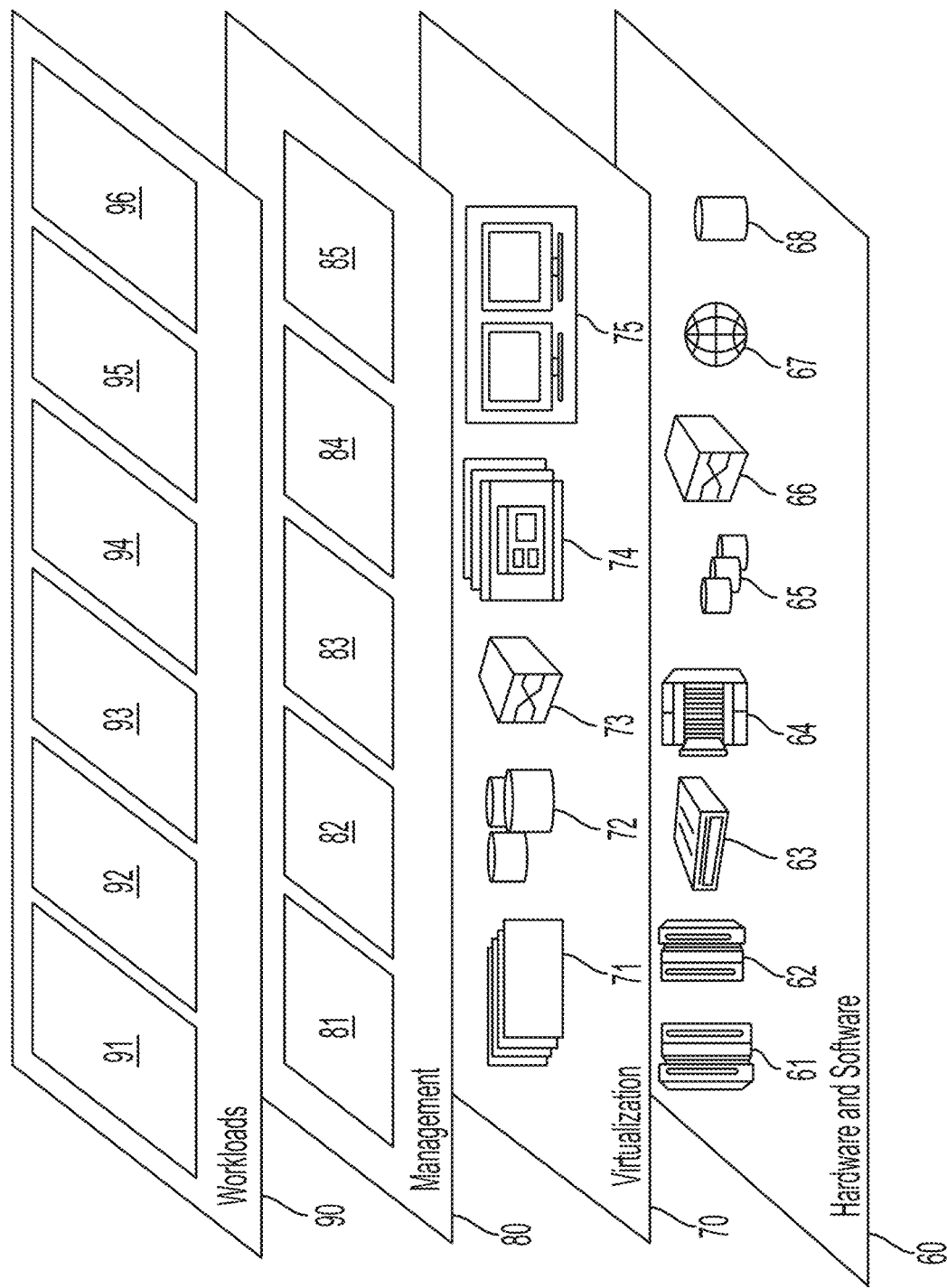
FIG. 9 depicts abstraction model layers according to one or more embodiments of the present invention.

Referring now to FIG. 9, a set of functional abstraction layers provided by cloud computing environment 50 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and breakpoint generation 96.

It is understood that one or more embodiments of the present invention are capable of being implemented in conjunction with any type of computing environment now known or later developed.

Turning now to FIG. 10, a computer system 1000 for handling form data in NLP is generally shown in accordance with one or more embodiments of the present invention. The methods described herein can be implemented in hardware, software (e.g., firmware), or a combination thereof. In one or more exemplary embodiments of the present invention, the methods described herein are implemented in hardware as part of the microprocessor of a special or general-purpose digital computer, such as a personal computer, workstation, minicomputer, or mainframe computer. The system 1000 therefore may include general-purpose computer or mainframe 1001 capable of running multiple instances of an O/S simultaneously.

In one or more exemplary embodiments of the present invention, in terms of hardware architecture, as shown in FIG. 10, the computer 1001 includes one or more processors 1005, memory 1010 coupled to a memory controller 1015, and one or more input and/or output (I/O) devices 1040, 1045 (or peripherals) that are communicatively coupled via a local input/output controller 1035. The input/output controller 1035 can be, for example but not limited to, one or more buses or other wired or wireless connections, as is known in the art. The input/output controller 1035 may have additional elements, which are omitted for simplicity, such as controllers, buffers (caches), drivers, repeaters, and receivers, to enable communications. Further, the local interface may include address, control, and/or data connections to enable appropriate communications among the aforementioned components. The input/output controller 1035 may include a plurality of sub-channels configured to access the output devices 1040 and 1045. The sub-channels may include fiber-optic communications ports.

The processor 1005 is a hardware device for executing software, particularly that stored in storage 1020, such as cache storage, or memory 1010. The processor 1005 can be any custom made or commercially available processor, a central processing unit (CPU), an auxiliary processor among several processors associated with the computer 1001, a semiconductor based microprocessor (in the form of a microchip or chip set), a macroprocessor, or generally any device for executing instructions.

The memory 1010 can include any one or combination of volatile memory elements (e.g., random access memory (RAM, such as DRAM, SRAM, SDRAM, etc.)) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 1010 may incorporate electronic, magnetic, optical, and/or other types of storage media. Note that the memory 1010 can have a distributed architecture, where various components are situated remote from one another, but can be accessed by the processor 1005.

The instructions in memory 1010 may include one or more separate programs, each of which comprises an ordered listing of executable instructions for implementing logical functions. In the example of FIG. 10, the instructions in the memory 1010 a suitable operating system (OS) 1011. The operating system 1011 essentially controls the execution of other computer programs and provides scheduling, input-output control, file and data management, memory management, and communication control and related services.

In accordance with one or more embodiments of the present invention, the memory 1010 may include multiple logical partitions (LPARs) each running an instance of an operating system. The LPARs may be managed by a hypervisor, which may be a program stored in memory 1010 and executed by the processor 1005.

In one or more exemplary embodiments of the present invention, a conventional keyboard 1050 and mouse 1055 can be coupled to the input/output controller 1035. Other output devices such as the I/O devices 1040, 1045 may include input devices, for example but not limited to a printer, a scanner, microphone, and the like. Finally, the I/O devices 1040, 1045 may further include devices that communicate both inputs and outputs, for instance but not limited to, a network interface card (NIC) or modulator/demodulator (for accessing other files, devices, systems, or a network), a radio frequency (RF) or other transceiver, a telephonic interface, a bridge, a router, and the like. The system 1000 can further include a display controller 1025 coupled to a display 1030.

In one or more exemplary embodiments of the present invention, the system 1000 can further include a network interface 1060 for coupling to a network 1065. The network 1065 can be an IP-based network for communication between the computer 1001 and any external server, client and the like via a broadband connection. The network 1065 transmits and receives data between the computer 1001 and external systems. In an exemplary embodiment, network 1065 can be a managed IP network administered by a service provider. The network 1065 may be implemented in a wireless fashion, e.g., using wireless protocols and technologies, such as WiFi, WiMax, etc. The network 1065 can also be a packet-switched network such as a local area network, wide area network, metropolitan area network, Internet network, or other similar type of network environment. The network 1065 may be a fixed wireless network, a wireless local area network (LAN), a wireless wide area network (WAN) a personal area network (PAN), a virtual private network (VPN), intranet or other suitable network system and includes equipment for receiving and transmitting signals.

If the computer 1001 is a PC, workstation, intelligent device or the like, the instructions in the memory 1010 may further include a basic input output system (BIOS) (omitted for simplicity). The BIOS is a set of essential software routines that initialize and test hardware at startup, start the OS 1011, and support the transfer of data among the hardware devices. The BIOS is stored in ROM so that the BIOS can be executed when the computer 1001 is activated.

When the computer 1001 is in operation, the processor 1005 is configured to execute instructions stored within the memory 1010, to communicate data to and from the memory 1010, and to generally control operations of the computer 1001 pursuant to the instructions. In accordance with one or more embodiments of the present invention, computer 1001 is an example of a cloud computing node 10 of FIG. 8.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

One or more of the methods described herein can be implemented with any or a combination of the following technologies, which are each well known in the art: a discreet logic circuit(s) having logic gates for implementing logic functions upon data signals, an application specific integrated circuit (ASIC) having appropriate combinational logic gates, a programmable gate array(s) (PGA), a field programmable gate array (FPGA), etc.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the actions can be performed in a differing order or actions can be added, deleted or modified. Also, the term "coupled" describes having a signal path between two elements and does not imply a direct connection between the elements with no intervening elements/connections therebetween. All of these variations are considered a part of the present disclosure.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method comprising:
    receiving a document at a processor;
    classifying, by the processor, at least a subset of the document as a style of a form of the at least a subset of the document, wherein the style is one of: a binary response form style, a checkbox form style, a circle selection form style, a radio button form style, an underline selection form, a questionnaire, or an unrecognized style of form;
    extracting features from the document, the extracting comprising:
        initiating processing of the at least a subset of the document by a first processing engine trained to extract features from the style;
        initiating processing of a remaining portion of the document not included in the at least a subset of the document by a second processing engine trained to extract features from a non-form-type of data; and
        receiving features from one or both of the first processing engine and the second processing engine;
    storing, by the processor, the received features as features of the document; and
    determining, via the first processing engine or the second processing engine, an accuracy weight of the features of the document based on an identity associated with a data entry of the form.

2. The method of claim 1, wherein the non-form-type of data is sentence or paragraph data.

3. The method of claim 1, further comprising combining the received features to generate combined features of the document, wherein the features of the document that are stored are the combined features of the document.

4. The method of claim 1, wherein the document is a healthcare document for a patient and the method further comprises associating the received features with the patient.

5. The method of claim 4, wherein the healthcare document is a medical record.

6. The method of claim 1, wherein the processing by one or both of the first processing engine and the second processing engine includes a natural language processing (NLP) engine.

7. The method of claim 1, further comprising converting the document to a text format prior to the classifying.

8. The method of claim 1, further comprising converting the document to an image format prior to the classifying.

9. The method of claim 1, wherein the classifying is performed by a classifier engine that was previously trained to identify data of the style.

10. The method of claim 1, further comprising:
    receiving a second document that does not include the style;
    extracting features from the second document, the extracting features from the second document comprising:
        initiating processing of the second document by the second processing engine; and
        receiving second features from the second processing engine; and
    storing, by the processor, the received second features as features of the second document.

11. A system comprising:
one or more processors for executing computer readable instructions, the computer readable instructions controlling the one or more processors to perform operations comprising:
receiving a document at a processor of the one or more processors;
classifying, by the processor, at least a subset of the document as a style of a form of the at least a subset of the document, wherein the style is one of: a binary response form style, a checkbox form style, a circle selection form style, a radio button form style, an underline selection form, a questionnaire, or an unrecognized style of form;
extracting features from the document, the extracting comprising:
initiating processing of the at least a subset of the document by a first processing engine trained to extract features from the style;
initiating processing of a remaining portion of the document not included in the at least a subset of the document by a second processing engine trained to extract features from a non-form-type of data; and
receiving features from one or both of the first processing engine and the second processing engine;
storing, by the processor, the received features as features of the document; and
determining, via the first processing engine or the second processing engine, an accuracy weight of the features of the document based on an identity associated with a data entry of the form.

12. The system of claim 11, wherein the non-form-type of data is sentence or paragraph data.

13. The system of claim 11, wherein the operations further comprise combining the received features to generate combined features of the document, wherein the features of the document that are stored are the combined features of the document.

14. The system of claim 11, wherein the document is a healthcare document for a patient and the method further comprises associating the received features with the patient.

15. The system of claim 14, wherein the healthcare document is a medical record.

16. The system of claim 11, wherein the processing by one or both of the first processing engine and the second processing engine includes natural language processing (NLP) engine.

17. The system of claim 11, wherein the classifying is performed by a classifier engine that was previously trained to identify the style in documents.

18. The system of claim 11, wherein the operations further comprise:
receiving a second document that does not include the style; and
extracting features from the second document, the extracting features from the second document comprising:
initiating processing of the second document by the second processing engine; and
receiving second features from the second processing engine; and
storing, by the processor, the received second features as features of the second document.

19. A computer program product comprising a computer readable storage medium having program instructions embodied therewith, the program instructions executable by one or more processors to cause the one or more processors to perform operations comprising:
receiving a document;
classifying, via a classifier engine, a first subset of the document;
identifying, via the classification engine, a style of a form of the first subset of the document as an output of the classification;
selecting a first processing engine based on the style, wherein the first processing engine is trained to extract features from the style;
extracting, via the first processing engine, a first set of features of the first subset of the document;
extracting, via a second processing engine trained to extract features from a non-form-type of data, a second set of features of a second subset of the document;
storing the first set of features and the second set of features; and
determining, via the first processing engine or the second processing engine, an accuracy weight of the features of the document based on an identity associated with a data entry of the form.

20. The computer program product of claim 19, wherein the non-form-type of data is sentence or paragraph data.

21. The computer program product of claim 19, wherein the style is one of: a binary response form, a checkbox form, a circle selection form, a radio button form, an underline selection form, a table, a list, or a questionnaire.

22. The computer program product of claim 19, the operations further comprising:
upon determining that the style is an unrecognized style, not processing the form via the first processing engine or the second processing engine.

23. The computer program product of claim 19, the operations further comprising:
upon determining that the identity identifies a patient, reducing the accuracy weight; and
discarding at least a portion of the features of the document based on the accuracy weight.

24. The computer program product of claim 19, the operations further comprising:
upon determining that the identity identifies a medical care provider, increasing the accuracy weight; and
retaining at least a portion of the features of the document based on the accuracy weight.

* * * * *